(12) United States Patent
Leung et al.

(10) Patent No.: US 6,326,390 B1
(45) Date of Patent: Dec. 4, 2001

(54) USE OF ADENOSINE $A_3$ RECEPTOR ANTAGONISTS TO INHIBIT TUMOR GROWTH

(75) Inventors: Edward Leung, Cary, NC (US); Pier Giovanni Baraldi; Pier Andrea Borea, both of Ferrara (IT); Shih-Fong Chen, Apex, NC (US)

(73) Assignee: King Pharmaceuticals Reseach and Development, Inc., Cary, NC (US)

( * ) Notice: Subject to any disclaimer, the term of this patent is extended or adjusted under 35 U.S.C. 154(b) by 0 days.

(21) Appl. No.: 09/377,271

(22) Filed: Aug. 19, 1999

Related U.S. Application Data
(60) Provisional application No. 60/097,852, filed on Aug. 25, 1998.

(51) Int. Cl.[7] .................................................. A61K 31/41
(52) U.S. Cl. ............................................................... 514/383
(58) Field of Search ............................................... 514/383

(56) References Cited

U.S. PATENT DOCUMENTS 5,916,911    6/1999    Shayman et al. ................... 514/428

OTHER PUBLICATIONS

Granger, C. B., M.D., "Adenosine for Myocardial Protection in Acute Myocardial Infarction", *Am. J. Cardiol*, 79(12A): 44–48, 1997.

Jacobson K. A., et al., "$A_3$–adenosine receptors: design of selective ligands and therapeutic prospects," *Drugs of the Future*, 20: 689–699, 1995.

Jacobson, K. A., et al., "Structure–Activity Relationships of 9–Alkyladenine and Ribose–Modified Adenosine Derivatives at Rat $A_3$ Adenosine Receptors," *J. Med. Chem.*, 38: 1720–1735, 1995.

Jacobson, K. A., et al., "Pharmacological Characterization of Novel $A_3$ Adenosine Receptor–Selective Antagonsts," *Neuropharmacology*, 36(9): 1157–1165, 1997.

Jiang J., et al., "6–Phenyl–1,4–dihydropyridine Derivatives as Potent and Selective $A_3$ Adenosine Receptor Anatagonists," *J. Med. Chem.*, 39: 4667–4675, 1996.

Jiang J., et al., "Structure–Activity Relationships of 4–(Pphenylethynyl)–6–phenyl–1,4–dihydropyridines as Highly Selective $A_3$ Adenosine Receptor Antagonists," *J. Med. Chem.*, 40: 2596–2608, 1996.

Karton, Y., et al., "Synthesis and Biological Activites of Flavonoid Derivatives as $A_3$ Adenosine Receptor Antagonists," *J. Med. Chem.*, 39: 2293–2301, 1996.

Kim, Y., et al., "Derivatives of the Triazoloquinazoline Adenosine Antagonist (CGS15943) Are Selective for the human $A_3$ Receptor Subtype," *J. Med. Chem.*, 39(21): 4142–4148, 1996.

Kohno, Y., et al., "Activation of Adenosine $A_3$ Receptors on Human Eeosinophils Elevates Intracellular Calcium," *Blood*, 88(9): 3569–3574, 1996.

Liang, B. T., et al., "A physiological role of the adenosine $A_3$ receptor: Sustained cardioproteciton", *Proc. Natl. Acad. Sci.*, 95: 6995–6999, 1998.

Siddiqi, S. M., et al., "A Survey of Non–xanthine Derivatives as Adenosine Receptor Ligands", *Nucleosides, Nucleotides*, 15(1–3): 693–718, 1996.

Stambaugh, K., et al., "A novel cardioprotective function of adenosine $A_1$ and $A_3$ receptors during prolonged simulated ischemia", *Am. J. of Physoilogy*, 273(1, part 2): H501–505, 1997.

Takagi, H., et al., "Adenosine mediates hypoxic Induction of Vascular Endothelial Growth Factor in Retinal Pericytes and Endothelial Cells", *Inves. Opthalmol. & Vis. Sci.*, 37(11), 2165–2176, 1996.

Van Rhee, A. M., et al., "Development of 1,4–Dihydropyridines as Selective $A_3$ Adenosine Receptors Antagonists," *Drug Devel. Res.*, 37(3): 131, 1996.

Van Rhee, A. M., et al., "Interaction of 1,4–Dihydropyridine and Pyridine Derivatives with adenosine Receptors: Selectivity for $A_3$ Receptors," *J. Med. Chem.*, 39: 2980–3989, 1996.

Van Rhee, A. M., et al., "Tetrahydrobenzothiophenone Derivatives as a Novel Class of Adenosine Receptor Antagonists," *J. Med Chem.*, 39: 398–406, 1996.

Yao, Y., et al., "Adenosine $A_3$ Receptor Agonist Pprotect HL–60 and U–937 Cells from Apoptosis Induced by $a_3$ Antagonists," *Biochem. Biophys. Res. Commun.*, 232: 317–322, 1997.

Windholz, M., "Cisplatin", The Merck Index, tenth edition, Merck 7 Co., Rahway, NJ, Abstract No. 2289, 1983.

*Primary Examiner*—Dwayne C. Jones
(74) *Attorney, Agent, or Firm*—Roberts Abokhair & Mardula, LLC (57) ABSTRACT

Tumor growth and metastasis can be inhibited by administration of adenosine $A_1$ and/or $A_3$ antagonists, preferably $A_3$ antagonists, to a patient. The antagonists can be, and preferably are, administered in combination with other anti-tumor agents, such as anti-angiogenic agents (including adenosine $A_{2a}$ antagonists) and/or cytotoxic agents. Because the cytotoxic agents attack the tumor cells themselves, and the anti-angiogenic agents prevent the growth of vasculature which would otherwise support the growth of the tumor cells.

39 Claims, 4 Drawing Sheets

USE OF ADENOSINE A₃ RECEPTOR ANTAGONISTS TO INHIBIT TUMOR GROWTH

This application claims benefit of Provisional Application No. 60/097,852 filed Aug. 25, 1998.

FIELD OF THE INVENTION

The present invention relates to the use of adenosine $A_3$ receptor antagonists to inhibit the growth of tumors.

BACKGROUND OF THE INVENTION

Traditional anti-tumor therapy has employed cytotoxic agents, such as cis-platin, vinblastine, daunorubicin, and doxorubicin, to inhibit tumor cell growth. Recently, agents that inhibit the growth of new blood vessels have been found to be effective anti-tumor agents when used alone or in combination with chemotherapy (see, for example, Nature, 394:297 (1998).

Inhibition of the growth of new blood vessels around a tumor can inhibit tumor growth because, in solid tumors, there is a need for an extensive vascular network to support tumor growth and metastasis. Solid tumors cannot grow beyond the size of a pinhead (1 to 2 cubic millimeters) without inducing the formation of new blood vessels to supply the nutritional needs of the tumor. When the blood supply is limited, tumor growth and metastasis is suppressed.

At a critical point in the growth of a tumor, the tumor sends out signals to the nearby endothelial cells to activate new blood vessel growth. Two endothelial growth factors, VEGF and basic fibroblast growth factor (bFGF), are expressed by many tumors and seem to be important in sustaining tumor growth.

Angiogenesis is also related to metastasis. It is generally true that tumors with higher densities of blood vessels are more likely to metastasize and are correlated with poorer clinical outcomes. Also, the shedding of cells from the primary tumor begins only after the tumor has a full network of blood vessels. In addition, both angiogenesis and metastasis require matrix metalloproteinases, enzymes that break down the surrounding tissue (the extracellular matrix), during blood vessel and tumor invasion.

Several anti-angiogenesis drugs function by targeting specific molecules involved in new blood vessel formation. For others, the exact mechanism of action is unknown, but the compounds have been shown to be anti-angiogenic by specific laboratory tests (in the test tube or in animals).

About 15 proteins are known to activate endothelial cell growth and movement, including angiogenin, epidermal growth factor, estrogen, fibroblast growth factors (acidic and basic), interleukin 8, prostaglandin $E_1$ and $E_2$, tumor necrosis factor-α, vascular endothelial growth factor (VEGF), and granulocyte colony-stimulating factor. However, most evidence points to a special role for VEGF (vascular endothelial growth factor). VEGF is a protein that is secreted from blood-deprived tissues and from some types of malignant cells.

VEGF appears to be important for tumor-induced vasculogenesis and enhanced vascular permeability. VEGF regulates angiogenesis by binding to specific receptors on nearby blood vessels, causing new vessels to form. Anti-VEGF agents have been proposed for inhibiting tumor growth.

One class of compounds which appears to be active against VEGF are anti-VEGF antibodies, including recombinant humanized monoclonal antibodies and chimeric antibodies. Sigma Chemicals commercially sells an anti-VEGF antibody (Human, clone no. 26503.11). Genentech's anti-VEGF and Agouron's AF3340 are also being investigated in various clinical trials. These antibodies purportedly have the ability to prevent VEGF from binding to its receptors.

Chimeric antibodies are antibodies in which an entire, intact, variable domain of a human antibody is substituted with that of a non-human one. In contrast, a humanized antibody includes only substitution of the six antigen-binding loops (CDRs) of the human antibody with those from a non-human one. Exchanging some non-CDR residues may also be required to attain binding of the humanized antibody that is similar to those of the parent non-human antibody.

Other known inhibitors of angiogenesis include angiostatin, endostatin, interferons, interleukin 1 (α and β), interleukin 12, retinoic acid, and tissue inhibitors of metalloproteinase-1 and -2. (TIMP-1 and -2). Small molecules, such as razoxane, a topoisomerase II inhibitor with anti-angiogenic activity, have also been investigated for their ability to inhibit tumor angiogenesis.

Genetic material, such as antisense oligonucleotides and aptamers which inhibit VEGF have also been developed. Numerous articles have been published regarding oligonucleotide aptamers which purportedly have anti-VEGF activity. However, major limitations associated with the use of aptamers is that the body has numerous mechanisms for destroying exogenous DNA, such as exo and endonucleases. Further, there are synthetic difficulties associated with preparing useful amounts of oligonucleotides such as the anti-VEGF aptamers. Still further, the ability of these compounds to bind useful sites in vivo has yet to be demonstrated in a human model, in part due to the difficulty in preparing the compounds in a scale sufficient for clinical studies, and also in part due to the inability to develop useful animal models, which is related to the purported high affinity of the compounds for the human target sites.

The differences between standard chemotherapy and anti-angiogenesis therapy result from the fact that angiogenesis inhibitors target dividing endothelial cells rather than tumor cells. Anti-angiogenic drugs are not likely to cause bone marrow suppression, gastrointestinal symptoms, or hair loss—symptoms characteristic of standard chemotherapy treatments. Also, since anti-angiogenic drugs may not necessarily kill tumors, but rather hold them in check indefinitely, the endpoint of early clinical trials may be different than for standard therapies. Rather than looking only for tumor response, it may be appropriate to evaluate increases in survival and/or time to disease progression.

Drug resistance is a major problem with chemotherapy agents. This is because most cancer cells are genetically unstable, are more prone to mutations and are therefore likely to produce drug resistant cells. Since angiogenic drugs target normal endothelial cells which are not genetically unstable, drug resistance may not develop. Finally, anti-angiogenic therapy may prove usefll in combination with therapy directly aimed at tumor cells. Because each therapy is aimed at a different cellular target, it is possible that the combination will prove more effective than either therapy alone. For these reasons, development of new anti-angiogenic agents remains an important goal for cancer research.

Adenosine is known to be released in hypoxia. Numerous studies have shown adenosine to protect cells in the heart from ischemic damage. Adenosine binds to different receptor sites in the body. Four types of receptors have been identified, including the $A_1$, $A_{2a}$, $A_{2b}$, and $A_3$ receptors.

Adenosine has been shown to have protective roles in numerous animal models and in man (*Am. J. Cardiol.* 79(12A):44–48 (1997). For example, in the heart, both the $A_1$ and $A_3$ receptors offer protection against ischemia (*Am. J. Physiol.*, 273(42)H501–505 (1997). However, it is the $A_3$ receptor that offers sustained protection against ischemia (PNAS 95:6995–6999 (1998). The ability of adenosine to protect tumor cells against hypoxia has not been recognized by others.

The $A_3$ receptor is believed to mediate processes of inflammation, hypotension, and mast cell degranulation, and apparently also has a role in the central nervous system. The $A_3$ selective agonist IB-MECA induces behavioral depression and upon chronic administration protects against cerebral ischemia. $A_3$ selective agonists at high concentrations were also found to induce apoptosis in HL-60 human leukemia cells. These and other findings have made the $A_3$ receptor a promising therapeutic target.

Selective antagonists for the $A_3$ receptor have been proposed for use as antiinflammatory and antiischemic agents in the brain. Recently, $A_3$ antagonists have been under development as antiasthnatic, antidepressant, antiarrhythmic, renal protective, antiparlinson and cognitive enhancing drugs.

Recent studies in myocytes have shown the adenosine $A_3$ receptors to be responsible for long term protection against ischemia (Liang and Jacobson, PNAS, 95:6995–6999 (1998)). While the present inventors have hypothesized that adenosine plays a protective role in other cell types, including tumor cells, in addition to myocytes, no efforts have been made to limit the protective effect of adenosine on tumor cells.

It is therefore an object of the present invention to provide compositions and methods of treatment of tumor cells which involve minimizing or eliminating the protective effect of adenosine on tumor cells.

SUMMARY OF THE INVENTION

Compounds which are antagonists of the adenosine $A_1$ or $A_3$ receptors, preferably the $A_3$ receptor, inhibit the protective effect of adenosine on growing tumor cells when such cells are starved of oxygen (i.e., before an adequate vasculature is developed, or when anti-angiogenesis agents are administered). The antagonists can bind in the same site as adenosine, or can be allosteric antagonists (i.e., they bind at a site different from where adenosine binds, but adversely effect the ability of adenosine to bind to the site or adversely affect the ability of adenosine, once bound to the $A_1$ or $A_3$ receptors, to protect growing tumor cells).

Administration of antagonists for the adenosine $A_1$ and $A_3$ receptors will antagonize the protective effects against hypoxia and render those cells susceptible to destruction due to hypoxia. Since the $A_1$ and $A_3$ receptors, in particular, the $A_3$ receptor, are responsible for sustained cellular protection against ischemia, antagonists for the $A_1$ or $A_3$ receptors are also effective as anti-tumor agents. In addition, adenosine has been shown to stimulate VEGF release via activation of the $A_{2a}$ receptor (Invest. Opthalmol Vis. Sci., 37:2165–2176 (1996). Therefore, antagonists for the $A_{2a}$ receptor, such as ZM241385 and SCH 5861 are effective at blocking the release of VEGF, and thus also have anti-tumor properties. $A_{2a}$ receptors are useful in treating solid tumors alone or in conjunction with conventional chemotherapy.

The compounds can be used in a method for inhibiting tumor growth in a mammal, including a human. The methods involve administering an effective amount of an adenosine $A_1$ or $A_3$ antagonists, preferably, $A_3$ antagonists sufficient to inhibit the ability of adenosine to protect tumor cells.

The compounds can be used in a pharmaceutical formulation that includes an adenosine $A_1$ and/or $A_3$ antagonist and one or more excipients. The formulations can also include other anti-tumor agents, including cytotoxic agents and other anti-angiogenesis agents. Adenosine $A_{2a}$ antagonists are an example of anti-angiogenesis agents. Other examples include anti-VEGF antibodies, both humanized and chimeric.

DETAILED DESCRIPTION OF THE INVENTION

Compounds which are antagonists of the adenosine $A_1$ or $A_3$ receptors, preferably the $A_3$ receptor, inhibit the protective effect of adenosine on growing tumor cells when such cells are starved of oxygen (i.e., before an adequate vasculature is developed, or when anti-angiogenesis agents are administered). The antagonists can bind in the same site as adenosine, or can be allosteric antagonists (i.e., they bind at a site different from where adenosine binds, but adversely effect the ability of adenosine to bind to the site or adversely affect the ability of adenosine, once bound to the $A_1$ or $A_3$ receptors, to protect growing tumor cells).

The compounds can be used in a method for inhibiting tumor growth in a mammal, including a human. The methods involve administering an effective amount of an adenosine $A_1$ and/or $A_3$ antagonist sufficient to inhibit the ability of adenosine to protect tumor cells.

The compounds can be used in a pharmaceutical formulation that includes an adenosine $A_1$ and/or $A_3$ antagonist and one or more excipients. The formulations can also include other anti-tumor agents, including cytotoxic agents and anti-angiogenesis agents, such as adenosine $A_{2a}$ antagonists.

Definitions

As used herein, a compound is an antagonist of an adenosine $A_3$ receptor if it is able to prevent the inhibition due to an agonist and is able to displace [$^{125}$I]-AB-MECA in a competitive binding assay.

As used herein, a compound is selective for the $A_3$ receptor if its affinity at the $A_3$ receptor is greater than its affinity at the $A_1$, $A_{2a}$ and $A_{2b}$ receptors. Preferably, the ratio of $A_1/A_3$ and $A_2/A_3$ activity is greater than about 50, preferably between 50 and 100, and more preferably, greater than about 100. Since the pharmacology at the $A_3$ receptor varies between species, especially between rodent $A_3$ and human $A_3$ receptors, it is important to determine the selectivity of the $A_3$ compounds in human adenosine receptors.

The same holds true for adenosine $A_1$ and $A_{2a}$ receptors in terms of whether they are selective.

Adenosine $A_1$ Antagonists

Adenosine $A_1$ antagonists are well known to those of skill in the art. Some of the more well known compounds include CPX, CVT 124, FK 352, and ILF 117, the structures of which are well known.

Adenosine $A_3$ Antagonists

Adenosine $A_3$ antagonists are well known to those of skill in the art. Some of the more well known compounds include MRS 1097, MRS 1191 and MRS 1220 (commercially available from Research Biochemicals International, Natick Mass.). Other suitable antagonists include those disclosed in Jacobson et al., *Neuropharmacology*, 36:1157–1165 (1997); Yao et al., *Biochem. Biophys. Res. Commun.*, 232:317–322 (1997); Kim et al., *J. Med. Chem.*, 39(21):4142–4148 (1996); van Rhee et al., *Drug Devel. Res.*, 37:131 (1996); van Rhee et al., *J. Med. Chem.*, 39:2980–2989 (1996); Siquidi et al., *Nucleosides, Nucleotides* 15:693–718 (1996); van Rhee et al., *J. Med. Chem.*, 39:398–406 (1996); Jacobson et al., *Drugs of the Future*, 20:689–699 (1995); Jacobson et al., *J. Med. Chem.*, 38:1720–1735 (1995); Karton et al., *J. Med. Chem.*, 39:2293–2301 (1996); Kohno et al., *Blood*, 88:3569–3574 (1996); Jiang et al., *J. Med. Chem.*, 39:4667–4675 (1996); Yao et al., *Biochem. Biophys. Res. Commun.* 232:317–322 (1997); and Jiang et al., *J. Med. Chem.* 40:2596–2608 (1996), the contents of which are hereby incorporated by reference in their entirety.

Cytotoxic and Anti-Angiogenic Agents

The $A_3$ antagonists can be administered alone or in combination with other anti-tumor agents, including cytotoxic/antineoplastic agents and anti-angiogenic agents. Cytotoxic/anti-neoplastic agents are defined as agents which attack and kill cancer cells.

Some cytotoxic/anti-neoplastic agents are alkylating agents, which alkylate the genetic material in tumor cells. These include cis-platin, cyclophospharnide, nitrogen mustard, trimethylene thiophosphoramide, carmustine, busulfan, chlorambucil, belustine, uracil mustard, chlornaphazin, and dacabazine.

Other cytotoxic/anti-neoplastic agents are antimetabolites for tumor cells. Examples of these types of agents include cytosine arabinoside, fluorouracil, methotrexate, mercaptopuirine, azathioprime, and procarbazine.

Other cytotoxic/anti-neoplastic agents are antibiotics. Examples include doxorubicin, bleomycin, dactinomycin, daunorubicin, mithramycin, mitomycin, mytomycin C, and daunomycin. There are numerous liposomal formulations commercially available for these compounds.

Still other cytotoxic/anti-neoplastic agents are mitotic inhibitors (vinca alkaloids). These include vincristine, vinblastine and etoposide.

Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. suitable anti-angiogenic agents include anti-VEGF antibodies, including humanized and chimeric antibodies, anti-VEGF aptamers and antisense oligonucleotides. Other known inhibitors of angiogenesis include angiostatin, endostatin, interferons, interleukin 1 ($\alpha$ and $\beta$), interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

In one embodiment, the anti-angiogenesis compound is an adenosine $A_{2a}$ antagonist. $A_{2a}$ antagonists are well known to those of skill in the art. Examples of these compounds include SCH 58261 from Schering Plough, ZM241385 (Palmer et al., *Mol. Pharmacol.*, 48:970–974 (1995), the tricyclic non-xanthine antagonists and the triazoloquinazolines, including CP 66,713, disclosed in Nikodijevic et al., *J. Pharmacol. Exp. Ther.*, 259:286–294 (1991), as well as the compounds disclosed in von Lubitz et al., *Eur. J. Pharmacol.*, 287:295–302 (1995). The contents of each of the references above are hereby incorporated by reference.

In a preferred embodiment, the composition includes an effective amount to inhibit tumor growth of an adenosine $A_3$ antagonist, a cytotoxic agent, and an anti-angiogenesis agent. The combination therapy will attack the tumor cell directly, inhibit growth of new blood vessels around the tumor cell, and, by virtue of the adenosine $A_3$ antagonists, inhibit the ability of the cell to survive without the growth of new blood vessels.

The compounds can be, and preferably are, administered in a time-release manner. Suitable time-release devices are well known to those of skill in the art. Examples include liposomes, microparticles, microcapsules, and nanoparticles. The microparticles can be prepared from biodegradable polymers, such that the duration of administration can be controlled.

Methods of Using the Compounds

The compounds can be used to treat solid tumors. Specific tumors which can be treated include fibrodysplasia ossificans progressiva, prostate cancer, benign prostatic hyperplasia, recessive dystrophic epidermolysis bullosa (RDEB), Lewis lung carcinoma, breast cancer, and brain tumors.

The compounds can be administered via any medically acceptable means. Suitable means of administration include oral, rectal, topical or parenteral (including subcutaneous, intravenous, intramuscular, intraperitoneal, and intra-arterial) administration, although oral or parenteral administration are preferred.

The amount of the adenosine $A_1$ and/or $A_3$ antagonist required to be effective will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective dose is in the range of about 0.1 $\mu$g/kg to about 10 mg/kg body weight per day, preferably in the range of about 1 mg/kg to about 3 mg/kg per day.

The total daily dose may be given as a single dose, multiple doses, e.g., two to six times per day, or by intravenous infusion for a selected duration. Dosages above or below the range cited above are within the scope of the present invention and may be administered to the individual patient if desired and necessary. For example, for a 75 kg mammal, a dose range would be about 75 mg to about 220 mg per day, and a typical dose would be about 150 mg per day. If discrete multiple doses are indicated, treatment might typically be 50 mg of a compound given 3 times per day.

Formulations

The compounds described above are preferably administered in formulation including an active compound, i.e., an adenosine $A_1$ and/or $A_3$ antagonist, together with an acceptable carrier for the mode of administration. Suitable pharmaceutically acceptable carriers are known to those of skill in the art.

The compositions can optionally include other therapeutically active agents, including anti-angiogenic and anti-cancer agents. Other optional ingredients include antivirals, antibacterials, anti-inflammatories, analgesics, and immunosuppresants. The carrier must be pharmaceutically acceptable in the sense of being compatible with the other ingredients of the formulation and not deleterious to the recipient thereof.

The formulations can include carriers suitable for oral, rectal, topical or parenteral (including subcutaneous, intramuscular and intravenous) administration. Preferred carriers are those suitable for oral or parenteral administration.

Formulations suitable for parenteral administration conveniently include sterile aqueous preparation of the active compound which is preferably isotonic with the blood of the recipient. Thus, such formulations may conveniently contain distilled water, 5% dextrose in distilled water or saline. Useful formulations also include concentrated solutions or solids containing the compounds which upon dilution with an appropriate solvent give a solution suitable for parental administration above.

For enteral administration, the compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

The compounds can also be administered locally by topical application of a solution, ointment, cream, gel, lotion or polymeric material (for example, a Pluronic™, BASF), which may be prepared by conventional methods known in the art of pharmacy. In addition to the solution, ointment, cream, gel, lotion or polymeric base and the active ingredient, such topical formulations may also contain preservatives, perfumes, and additional active pharmaceutical agents.

Formulations for rectal administration may be presented as a suppository with a conventional carrier, e.g., cocoa butter or Witepsol S55 (trademark of Dynamite Nobel Chemical, Germany), for a suppository base.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," *Drug Carriers in Biology and Medicine*, pp. 287–341 (Academic Press, 1979). Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925, 673 and 3,625,214, the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

In one embodiment, the compounds are administered intravenously in a liposome or microparticle with a size such that the particle can be delivered intraveneously, but gets trapped in a capillary bed around a growing tumor. Suitable particle sizes for this embodiment are those currently used, for example, in liposomes sold under the name DaunoXome™, which are believed to be between about 200 and 500 $\mu$m. The compounds are then released locally, over time, at the location of the tumor. This can be effective in limiting systemic effects of the administration of cytotoxic agents, and also targets the adenosine antagonist and any other anti-angiogenic agents directly to the site at which blood vessel growth is to be inhibited.

In another embodiment, the compounds are administered in a tissue coating, preferably a polymeric tissue coating, more preferably, a biodegradable tissue coating, which is applied to the site at which a tumor is surgically removed. Suitable polymeric materials are disclosed, for example, in U.S. Pat. No. 5,410,016 to Hubbell et al., the contents of which are hereby incorporated by reference.

The polymeric barrier, in combination with the adenosine $A_3$ antagonists, and optionally in combination with other anti-angiogenic agents and/or cytotoxic agents, provides a physical barrier as well as a chemical barrier to further tumor growth and vasculation around the tumor.

The two embodiments described above can be particularly useful when cytotoxic agents with pronounced systemic side effects are used. By targeting the administration of these compounds to a specific site, and locally delivering the compounds, systemic effects can be minimized.

In yet another embodiment, anti-VEGF antibodies can be covalently coupled to microparticles or liposomes including the compounds. The antibodies can be used to not only target the delivery of the compounds, but also to assist in inhibiting tumor growth by inhibiting angiogenesis.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

In addition to the aforementioned ingredients, the formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

Determination of the Degree of Activity for the Compounds The activity and selectivity of the compounds as adenosine $A_3$ antagonists can be readily determined using no more than routine experimentation using any of the following assays. Since the $A_1$ and $A_{2a}$ receptors express similar pharmacology between humans and rodents, endogenous receptors from the rat can be used for the $A_1$ and $A_{2a}$ binding assays.

Rat $A_1$ and $A_{2A}$ Adenosine Receptor Binding Assay

Membrane preparations:

Male Wistar rats (200–250 g) can be decapitated and the whole brain (minug brainstem, striatum and cerebellum) dissected on ice. The brain tissues can be disrupted in a Polytron (setting 5) in 20 vols of 50 mM Tris HCl, pH 7.4. The homogenate can then be centrifuged at 48,000 g for 10 min and the pellet resuspended in Tris-HCL containing 2 IU/ml adenosine deaminase, type VI (Sigma Chemical Company, St. Louis, Mo., USA). After 30 min incubation at 37° C., the membranes can be centrifuged and the pellets stored at −70° C. Striatal tissues can be homogenized with a Polytron in 25 vol of 50 mM Tris HCl buffer containing 10 mM $MgCl_2$ pH 7.4. The homogenate can then be centrifuged at 48,000 g for 10 min at 4° C. and resuspended in Tris HCl buffer containing 2 IU/ml adenosine deaminase. After 30 min incubation at 37° C., membranes can be centrifuged and the pellet stored at −70° C.

Radioligand binding assays:

Binding of [$^3$H]-DPCPX (1,3-dipropyl-8-cyclopentylxanthine) to rat brain membranes can be performed essentially according to the method previously described by Bruns et al., *Proc. Natl. Acad. Sci.* 77, 5547–5551 1980. Displacement experiments can be performed in 0.25 ml of buffer containing 1 nM [$^3$H]-DPCPX, 100 μl of diluted membranes of rat brain (100 μg of protein/assay) and at least 6–8 different concentrations of examined compounds. Non specific binding can be determined in the presence of 10 μM of CHA ($N^6$cyclohexyladenosine) and this is always ≦10% of the total binding. Incubation times are typically 120 min at 25° C.

Binding of [$^3$H]-SCH 58261 (5-amino-7-(2-phenylethyl)-2-(2-furyl)-pyrazolo[4,3-e]-1,2,4-triazolo[1,5-c]pyrimidine) to rat striatal membranes (100 μg of protein/assay) can be performed according to methods described in Zocchi et al., *J. Pharm. and Exper. Ther.* 276:398–404 (1996). In competition studies, at least 6–8 different concentrations of examined compounds should be used. Non specific binding can be determined in the presence of 50 μM of NECA (5'-(N-ethylcarboxamido)adenosine). Incubation time is typically 60 min at 25° C.

Bound and free radioactivity can be separated by filtering the assay mixture through Whatman GF/B glass-fiber filters using a Brandel cell harvester (Gaithersburg, Md., USA). The incubation mixture can be diluted with 3 ml of ice-cold incubation buffer, rapidly vacuum filtered and the filter can be washed three times with 3 ml of incubation buffer. The filter bound radioactivity can be measured, for example, by liquid scintillation spectrometry. The protein concentration can be determined, for example, according to a Bio-Rad method (Bradford, *Anal. Biochem.* 72:248 (1976)) with bovine albumin as reference standard.

Human cloned $A_3$ Adenosine Receptor Binding Assay

Receptor binding assays: Binding assays can be carried out according to methods described in Salvatore et al., *Proc. Natl. Acad. Sci.* 90:10365–10369 (1993). In saturation studies, an aliquot of membranes (8 mg protein/ml) from HEK-293 cells transfected with the human recombinant $A_3$ adenosine receptor (Research Biochemical International, Natick, Mass., USA) can be incubated with 10–12 different concentrations of [$^{125}$I]AB-MECA ranging from 0.1 to 5 nM. Competition experiments can be carried out in duplicate in a final volume of 100 μl in test tubes containing 0.3 nM [$^{125}$I]AB-MECA, 50 mM Tris HCl buffer, 10 mM $MgCl_2$, pH 7.4 and 20 μl of diluted membranes (12.4 mg protein/ml) and at least 6–8 different concentrations of examined ligands. Incubation time was 60 min at 37° C., according to the results of previous time-course experiments. Bound and free radioactivity were separated by filtering the assay mixture through Whatman GF/B glass-fiber filters using a Brandel cell harvester. Non-specific binding was defined as binding in the presence of 50 μM R-PIA and was about 30% of total binding. The incubation mixture was diluted with 3 ml of ice-cold incubation buffer, rapidly vacuum filtered and the filter was washed three times with 3 ml of incubation buffer. The filter bound radioactivity was counted in a Beckman gamma 5500B γ counter. The protein concentration can be determined according to a Bio-Rad method (3) with bovine albumin as reference standard.

Data Analysis

Inhibitory binding constant, $K_i$, values can be calculated from those of $IC_{50}$ according to the Cheng & Prusoff equation (Cheng and Prusoff, *Biochem. Pharmacol.* 22:3099–3108 (1973)), $K_i=IC_{50}/(1+[C^*]/K_D^*)$, where $[C^*]$ is the concentration of the radioligand and $K_D^*$ its dissociation constant.

A weighted non linear least-squares curve fitting program LIGAND (Munson and Rodbard, *Anal. Biochem.* 107:220–239 (1990)) can be used for computer analysis of saturation and inhibition experiments. Data are typically expressed as geometric mean, with 95% or 99% confidence limits in parentheses.

Animal Models

The efficacy of the compounds can be tested in animal models. For example, the efficacy of the adenosine $A_3$ antagonists alone or in combination with conventional anti-tumor agents such as cytotoxic/anti-neoplastic agents and anti-angiogenic agents can be compared to the conventional agents alone. Typically, a tumor of a given size is present in a rat or mouse. The mouse is treated with the agent and the size of the tumor is measured over time. The mean survival time of the animals can also be measured.

The adenosine $A_3$ antagonists which are used must actively bind the adenosine $A_3$ receptor in the animal which is to be tested. Xenografts can be implanted into the animal to test the ability of species specific cytotoxic compounds. However, the effect of the anti-angiogenic therapy depends on how well the anti-angiogenetic compounds work on inhibiting the specific animal's vasculation.

Assay methods that have demonstrated the efficacy of endostatin and angiostatin in suppressing tumor growth can be applied to A1, A3a, and A3 antagonists. For example, Lewis lung carcinoma, T241 fibrosarcoma or B16F10 melanoma can be grafted to mice (Nature, 390:404–407 (1997). Other tumors, such as PC-3 human prostate carcinoma, the CCL188 human colon carcinoma and the UBC urinary bladder carcinoma have been shown to release angiogenic agents (Cancer Res., 55:4230–4322 (1995). these tumors can also be grafted in mice for the evaluation of anti-tumor activities of adenosine antagonists. Adenosine antagonists can be administered to mice by the methods disclosed herein. This therapy can be used alone or in conjunction with anti-angiogenic therapy or conventional chemotherapy.

EXAMPLES

The following examples illustrate aspects of this invention but should not be construed as limitations. The symbols and conventions used in these examples are intended to be consistent with those used in the contemporary, international, chemical literature, for example, the *Journal of the American Chemical Society* ("J.Am.Chem.Soc.") and *Tetrahedron.*

Example 1

Evaluation of Biological Activity

Compound 1 (described above) has been tested for its affinity at rat $A_1$ and $A_{2A}$ and human $A_3$ receptors using the following assays.

Rat $A_1$ and $A_{2A}$ Adenosine Receptor Binding Assay

Male Wistar rats (200–250 g) were decapitated and the whole brain and striatum dissected on ice. The tissues were disrupted in a polytron homogenizer at a setting of 5 for 30 s in 25 volumes of 50 mM Tris HCl, pH 7.4, containing 10 mM $MgCl_2$. The homogenate was centrifuged at 48,000 for 10 min, and the pellet was resuspended in the same buffer containing 2 IU/mL adenosine deaminase. After 30 min incubation at 37° C., the membranes were centrifuged and pellets were stored at −80° C. Prior to freezing, an aliquot of homogenate was removed for protein assay with bovine albumin as reference standard. Binding assays were performed on rat brain and striatum membranes respectively, in the presence of 10 mM $MgCl_2$ at 25° C. All buffer solutions were adjusted to maintain a constant pH of 7.4.

Displacement experiments were performed in 500 µL of Tris HCl buffer containing 1 nM of the selective adenosine $A_1$ receptor ligand [$^3$H]CHA ($N^6$-cyclohexyladenosine) and membranes of rat brain (150–200 µg- of protein/assay).

Displacement experiments were performed in 500 µL of Tris HCl buffer containing 10 mM $MgCl_2$, 0.2 nM of the selective adenosine $A_{2A}$ receptor ligand [$^3$H]SCH58261 (5-amino-7-(2-phenylethyl)-2(2-furyl)-pyrazolo[4,3-e]-1,2,4-triazolo[1,5-c]pyrimidine) and membranes of rat striatum (80–100 µg of protein/assay). To determine $IC_{50}$ values (where $IC_{50}$ is the inhibitor concentration displacing 50% of labeled ligand) the test compound was added in triplicate to binding assay samples at a minimum of six different concentrations. Separation of bound from free radio ligand was performed by rapid filtration through Whatman GF/B filters which were washed three times with ice-cold buffer. Filter bound radioactivity was measured by scintillation spectrometry after addition of 5 mL of Aquassure. Non specific binding was defined as binding in the presence of 10 µM R-PIA ($N^6$-(phenylisopropyl)adenosine) and 10 µM NECA (5'-(N-ethylcarboxamido) adenosine), respectively, and was always 10% of the total binding. Incubation time ranged from 150 min. at 0° C. to 75 min at 30° C. according to the results of previous time-course experiments. Ki values were calculated from the Cheng-Prusoff equation. All binding data were analyzed using the nonlinear regression curve-fitting computer program LIGAND.

Human Cloned $A_3$ Adenosine Receptor Binding Assays.

Figure 1:
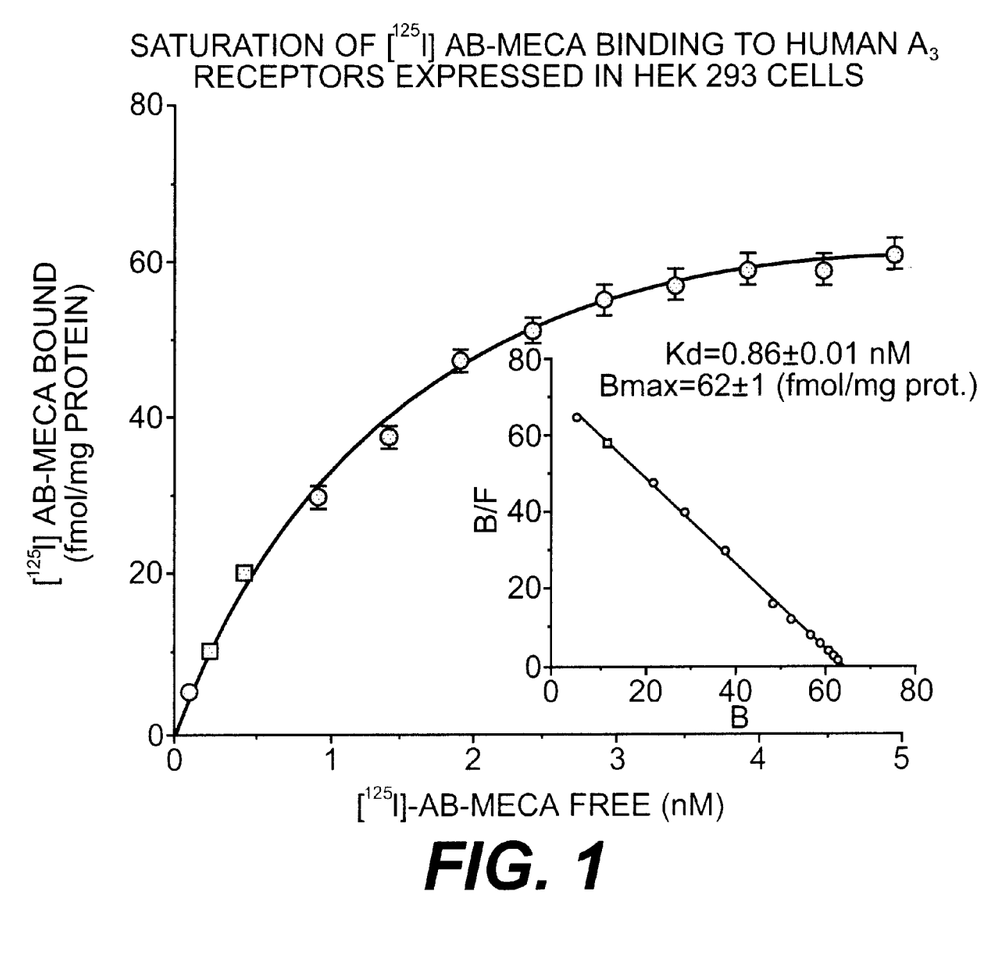
FIG. 1 is a graph showing the saturation of $[^{125}I]AB$-MECA binding (fmol/mg protein) to human $A_3$ receptors expressed in HEK 293 cells versus the molar concentration of $[^{125}I]AB$-MECA.

An aliquot of membranes (8 mu of protein/mL) from HEK-293 cells transfected with the human recombinant $A_3$ adenosine receptor was used for binding assays. FIG. 1 shows a typical saturation of [$^{125}$I]AB-MECA ($N^6$-(4-amino-3-iodobenzyl)-5'-(N-methylcarbamoyl)adenosine) to HEK-293 cells. Inhibition experiments were carried out in duplicate in a final volume of 100 µL in test tub containing 0.3 µM [$^{125}$I]AB-MECA, 50 nM Tris HCl buffer, 10 mM $MgCl_2$, pH 7.4, 20 µL of diluted membranes (12.4 mg of protein/mL), and at least 6–8 different concentrations of typical adenosine receptor antagonists. Non-specific binding was defined in the presence of 50 µM R-PIA and was about 30% of total binding. Incubation time was 60 min at 37° C., according to the results of previous time-course experiments. Bound and free radioactivity was separated by filtering the assay mixture through Whatman GF/B glass-fiber filters using a Brandel cell harvester.

Results and Discussion

The compounds was tested in radio ligand binding assays for affinity at rat brain $A_1$, $A_{2A}$ and human $A_3$ receptors. The results are shown below in Table 1.

TABLE 1

| Binding affinity at $rA_1$, $rA_{2A}$ and $hA_3$ adenosine receptors | | | | |
|---|---|---|---|---|
| $rA_1$ ($K_i$, nM) | $rA_{2A}$ ($K_i$, nM) | $hA_3$ ($K_i$, nM) | $rA_1/hA_3$ | $rA_{2A}/hA_3$ |
| >10,000 | 1,993 (1,658–2,397) | 0.29 (0.27–0.32) | >34,482 | 6,872 |

FIG. 1 shows a saturation curve of [$^{125}$I]AB-MECA to adenosine $A_3$ receptor and the linearity of the Scatchard plot in the inset is indicative, in our experimental conditions, of the presence of a single class of binding sites with $K_D$ value of 0.9±0.01 nM and Bmax value of 62±1 fmol/mg protein (n=3).

The data demonstrates that compound 1 showed relatively high affinity and selectivity for the human adenosine $A_3$ receptor subtype (h $A_3$).

Example 2

Binding Experiments With a Radiolabeled Compound

A series of binding experiments were performed on various tumor cell lines, using 0.5 mM [$^{125}$I]-ABMECA, with unspecific binding determined in the presence of 50 µM R-PIA or 200 µM NECA, on cell membranes of the cell lines. Specific binding was determined by substracting unspecific binding from total binding. The cell lines were the HL 60, NB4, SKN-MC, SKN-Be2C, SKN-SH and JURKAT cell lines. The results of the binding experiments are shown below in Table 2.

TABLE 2

| Cell Lines | Total Binding | Unspecific Binding | Specific Binding (cpm) | Percent Specific Binding |
|---|---|---|---|---|
| HL 60 | 3484 | 2791 | 693 | 20 |
| NB4 | 3377 | 2740 | 637 | 19 |
| SKN-MC | 7528 | 6220 | 1308 | 17 |
| SKN-Be2C | 6000 | 4585 | 1415 | 24 |
| SKN-SH | 2671 | 2580 | 91 | 3 |
| JURKAT | 7599 | 4753 | 2846 | 38 |

Figure 2:
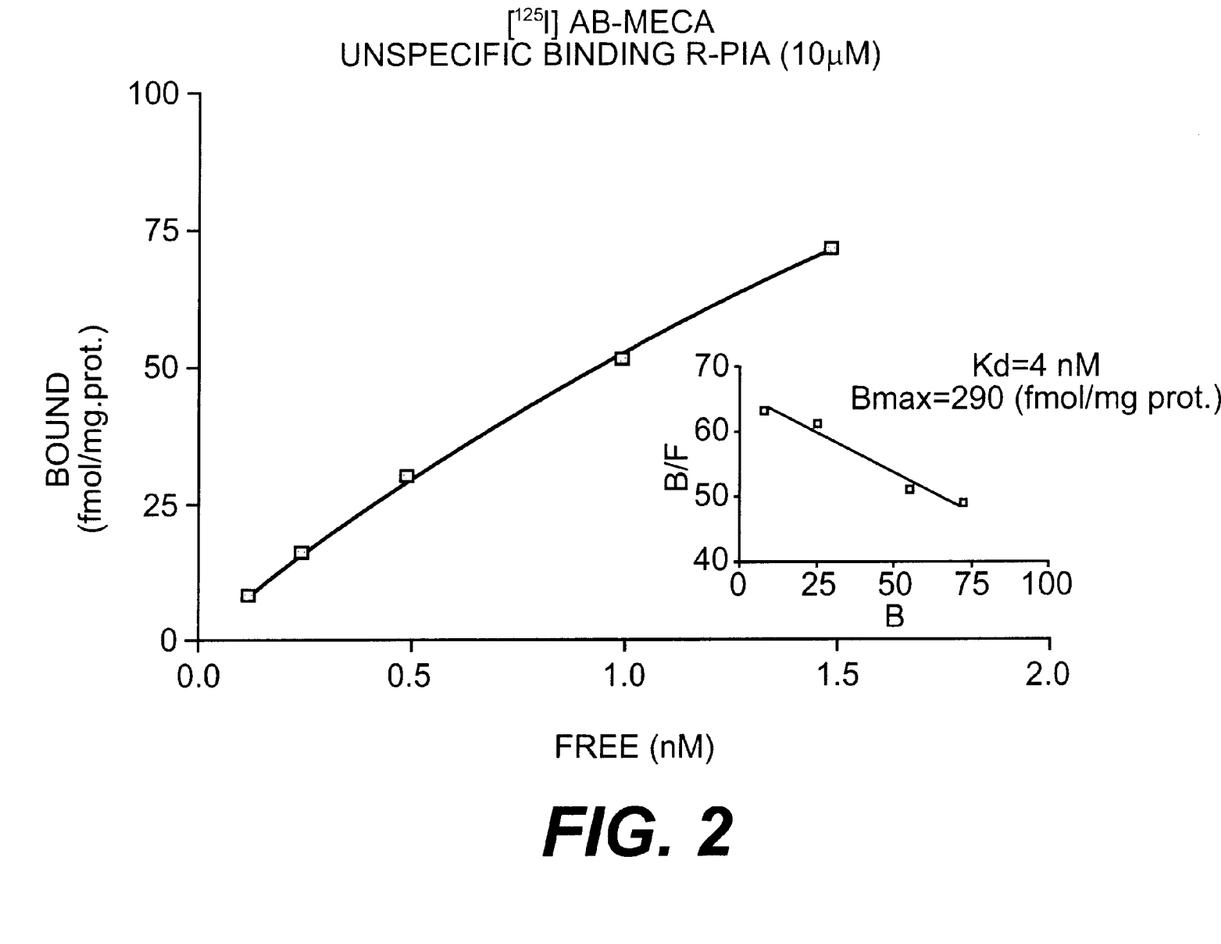
FIG. 2 is a graph showing the saturation of $[^{125}I]AB$-MECA binding (fmol/mg protein) to human $A_3$ receptors expressed in the JURKAT cell line versus the molar concentration of $[^{125}I]AB$-MECA. As shown in the Figure, the density of $A_3$ receptor detected was approximately 300 fmol/mg protein in Jurkat cell membranes using $[^{125}I]AB$-MECA.

The results are shown in graphical form in FIG. 2.

Jurkat cell lines appeared to provide the best results of the cell lines tested. A saturation experiment was performed using Jurkat cell lines at 37° C., with a one hour incubation period, using [$^{125}$I]-ABMECA (0.125–1.5 nM), with non-specific binding measured using RPIA (50 $\mu$M). The Kd (nM) was 4, and the Bmax (fmol/mg protein) was 290. The results are also shown in FIG. 2.

Another assay was performed to determine whether $A_1$ receptor were present. A displacement assay was performed at 0° C. for 150 minutes on Jurkat cells using [$^3$H] DPCPX, a specific $A_1$ antagonist (0.5 nM), with nonspecific binding determined using R-PIA (50 $\mu$M ). The total binding was 13208, the nonspecific binding was 2997, and the specific binding was 10211 (77%). Accordingly, a significant amount of $A_1$ binding was observed.

Figure 3:
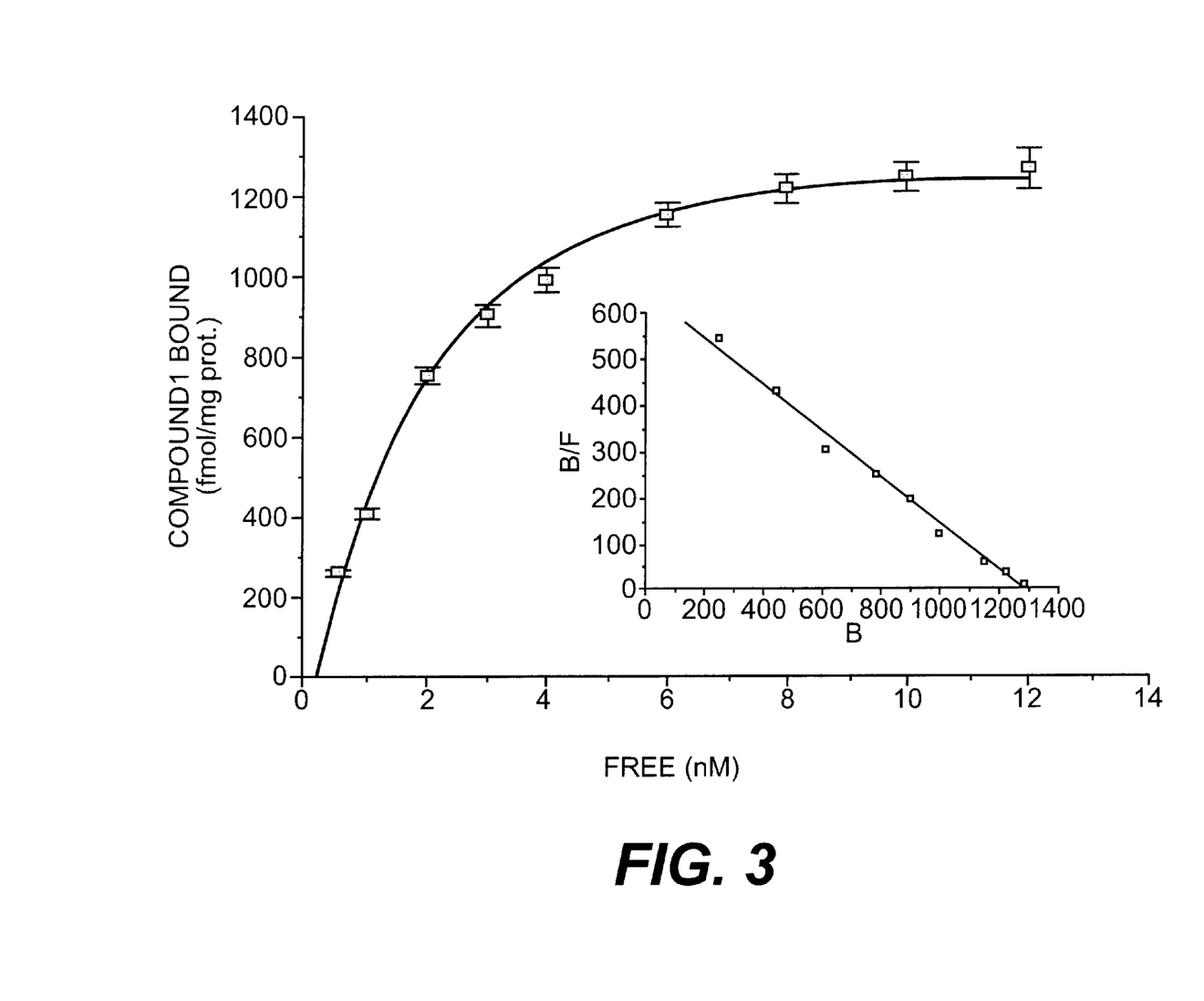
FIGS. 3 and 4 are graphs showing the saturation of the binding of a tritiated analogue of 5-[[(4-Methoxyphenyl)amino]carbonyl]amino-8-propyl-2-(2-furyl)-pyrazolo[4,3-e] 1,2,4-triazolo[1,5-c]pyrimidine (Compound 1) (fmol/mg protein) to $A_3$ receptors expressed in the JURKAT cell line versus the molar concentration of compound 1. The data in these figures show the presence of adenosine $A_3$ receptors in human tumor cells in high densities. For example, approximately 1300 fmol/mg protein was detected in Jurkat cells and 650 fmol/mg protein was detected in HL60 cells. Therefore, compound 1 is a far more sensitive tool for detecting adenosine $A_3$ receptors than $[^{125}I]AB$-MECA. These findings have facilitated the determination of the presence of $A_3$ receptors in many human tumors.
Figure 4:
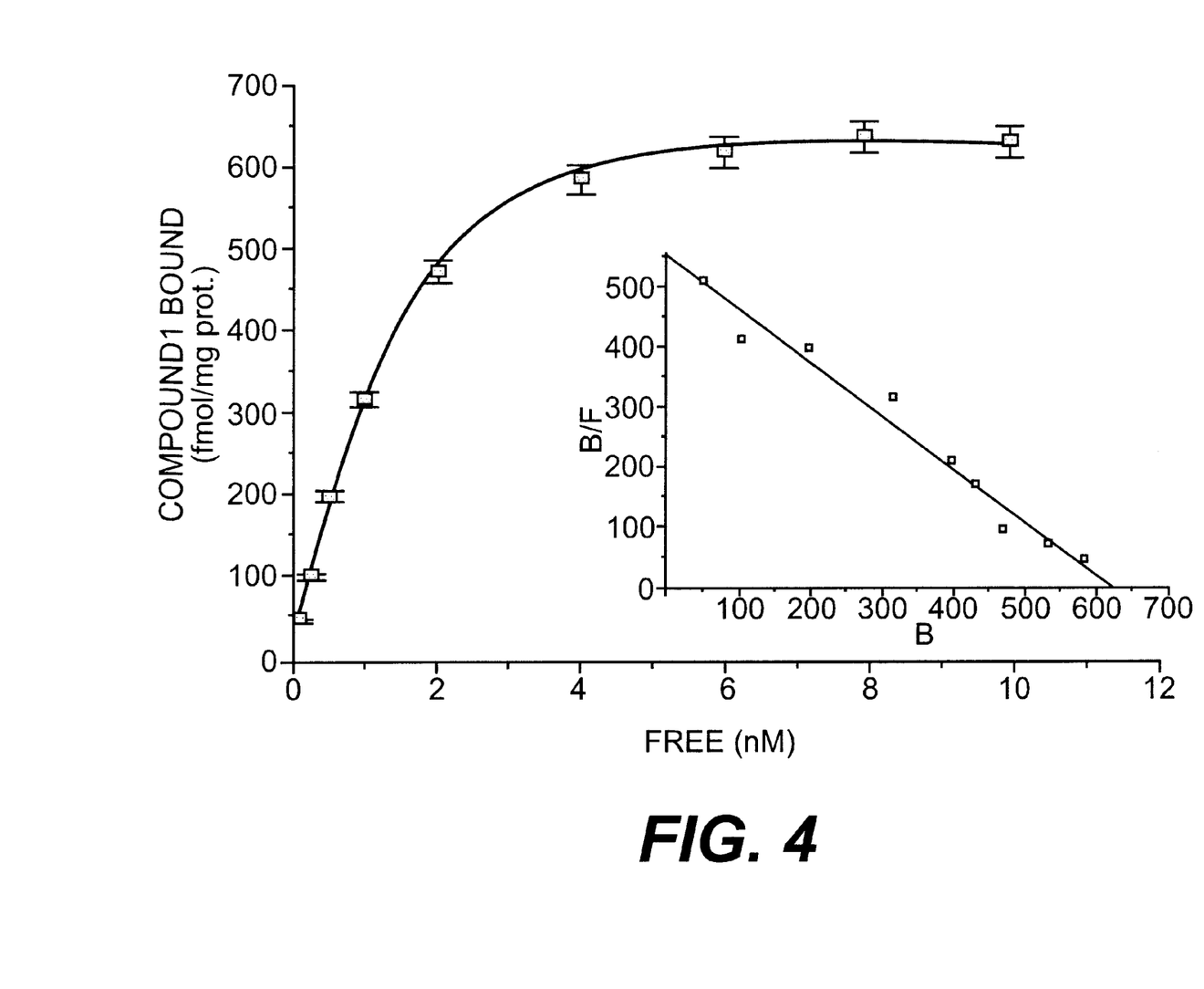

The following experiments described for the first time, the characterization of $A_3$ receptors in some human tumor cell lines such as HL60, a promyelocytic human leukaemia and Jurkat, a human T-cell leukaemia, by using the selective antagonist (Compound 1) described herein. In these studies, membranes (0.5 mg protein/ml) from Jurkat and HL60 cells were incubated with 10–12 different concentrations of the compound described above ranging from 0.2 to 15 nM and 0.1 to 10 nM for Jurkat and HL60 cells, respectively. FIG. 3 shows a saturation curve of the compound binding to adenosine $A_3$ receptors in Jurkat cell membranes and the linearity of the Scatchard plot in the inset is indicative of the presence of a single class of binding sites with a Kd value of 1.9±0.2 nM and $B_{max}$ value of 1.30±0.03 pmol/mg protein (n=3). FIG. 4 shows a saturation curve of compound 1 binding to adenosine $A_3$ receptors in HL60 membranes and the linearity of the Scatchard plot in the inset is indicative of the presence of a single class of binding sites with a Kd value of 1.2±0.1 nM and $B_{max}$ value of 626±42 fmol/mg protein (n=3).

These results show that many cell lines contain relatively large numbers of adenosine receptors. Because compound 1 is known to bind $A_3$ receptors with a high affinity and selectivity, it is likely that there is a relatively large presence of $A_3$ receptors in tumor cells.

Example 3

Pharmaceutical Formulations

| Ingredients | Amount |
|---|---|
| (A) Transdermal System - for 1000 patches | |
| Active compound | 100 g |
| Silicone fluid | 450 g |
| Colloidal silicon dioxide | 2 g |

| Ingredients | Amount |
|---|---|
| (B) Oral Tablet - For 1000 Tablets | |
| Active compound | 50 g |
| Starch | 50 g |
| Magnesium Stearate | 5 g |

The active compound and the starch are granulated with water and dried. Magnesium stearate is added to the dried granules and the mixture is thoroughly blended. The blended mixture is compressed into tablets.

| Ingredients | Amount |
|---|---|
| (C) Injection - for 1000, 1 mL Ampules | |
| Active compound | 10 g |
| Buffering Agents | q.s. |
| Propylene glycol | 400 mg |
| Water for injection | q.s. 1000 mL |

The active compound and buffering agents are dissolved in the propylene glycol at about 50° C. The water for injection is then added with stirring and the resulting solution is filtered, filled into ampules, sealed and sterilized by autoclaving.

| Ingredients | Amount |
|---|---|
| (D) Continuous Injection - for 1000 mL | |
| Active compound | 10 g |
| Buffering agents | q.s. |
| Water for injection | q.s. 1000 mL |

Those skilled in the art will recognize, or be able to ascertain using no more than routine experimentation, many equivalents to the specific embodiments of the invention described herein. Such equivalents are intended to be encompassed by the following claims.

What is claimed is:

1. A method for inhibiting tumor growth, comprising administering to a patient in need of treatment thereof an effective amount of an adenosine $A_1$ and/or $A_3$ antagonist to inhibit tumor growth.

2. The method of claim 1 wherein the antagonist is an adenosine $A_3$ antagonist.

3. The method of claim 1 wherein a cytotoxic agent is administered along with the antagonist.

4. The method of claim 1 wherein another anti-angiogenic agent is administered along with the antagonist.

5. The method of claim 4 wherein the agent is an anti-VEGF antibody.

6. The method of claim 1 wherein the antagonist is administered in a controlled release device.

7. The method of claim 1 wherein the controlled release device is a liposome or microparticle of a size which can be administered intraveneously but which lodges the liposome or microparticle in a capillary bed.

8. The method of claim 1 wherein the controlled release device is a tissue coating which is administered locally to a tissue surface.

9. The method of claim 8 wherein the polymer is biodegradable.

10. The method of claim 8 wherein the tissue surface is an area around which a tumor has been excised.

11. The method of claim 4 wherein the anti-angiogenic compound is an adenosine $A_{2a}$ antagonist.

12. A composition for inhibiting tumor growth comprising an adenosine $A_3$ antagonist in combination with a cytotoxic agent.

13. The composition of claim 12, wherein the composition is encapsulated in a microparticle or a liposome.

14. The composition of claim 13 wherein the microparticle or liposome is of a size which causes the particle to lodge in a capillary bed following intravenous administration.

15. The composition of claim 12, wherein the composition is present in a polymeric tissue coating.

16. The composition of claim 12, further comprising an anti-angiogenic agent.

17. The composition of claim 16, wherein the anti-angiogenic agent is an adenosine $A_{2a}$ antagonist.

18. A composition for inhibiting tumor growth comprising an adenosine $A_3$ antagonist in combination with an anti-angiogenic agent.

19. The composition of claim 18 wherein the anti-angiogenic agent is an adenosine $A_{2a}$ antagonist.

20. A method for inhibiting tumor growth, comprising administering to a patient in need of treatment thereof a dosage of an adenosine $A_1$ and/or $A_3$ antagonist to inhibit tumor growth of from 0.1 μg/kg to 10 mg/kg per day.

21. The method of claim 20 wherein the dosage of antagonist is from 1 mg/kg to 3 mg/kg per day.

22. The method of claim 20 wherein the antagonist is an adenosine $A_3$ antagonist.

23. The method of claim 20 wherein a cytotoxic agent is administered along with the antagonist.

24. The method of claim 20 wherein another anti-angiogenic agent is administered along with the antagonist.

25. The method of claim 24 wherein the agent is an anti-VEGF antibody.

26. The method of claim 20 wherein the antagonist is administered in a controlled release device.

27. The method of claim 20 wherein the controlled release device is a liposome or microparticle of a size which can be administered intravenously but which lodges the liposome or microparticle in a capillary bed.

28. The method of claim 20 wherein the controlled release device is a tissue coating which is administered locally to a tissue surface.

29. The method of claim 28 wherein the polymer is biodegradable.

30. The method of claim 28 wherein the tissue surface is an area around which a tumor has been excised.

31. The method of claim 24 wherein the anti-angiogenic compound is an adenosine $A_{2a}$ antagonist.

32. A composition for inhibiting tumor growth comprising a dosage of an adenosine $A_3$ antagonist in combination with a cytotoxic agent wherein the dosage of $A_3$ antagonist is from 0.1 μg/kg to 10 mg/kg per day.

33. The composition of claim 32 wherein the composition is encapsulated in a microparticle or a liposome.

34. The composition of claim 33 wherein the microparticle or liposome is of a size which causes the particle to lodge in a capillary bed following intravenous administration.

35. The composition of claim 32 wherein the composition is present in a polymeric tissue coating.

36. The composition of claim 32 further comprising an anti-angiogenic agent.

37. The composition of claim 36 wherein the anti-angiogenic agent is an adenosine $A_{2a}$ antagonist.

38. A composition for inhibiting tumor growth comprising a dosage of an adenosine $A_3$ antagonist in combination with an anti-angiogenic agent wherein the dosage of $A_3$ antagonist is from 0.1 μg/kg to 10 mg/kg per day.

39. The composition of claim 38 wherein the anti-angiogenic agent is an adenosine $A_{2a}$ antagonist.

* * * * *